United States Patent [19]

Reeder et al.

[11] Patent Number: 4,964,984

[45] Date of Patent: Oct. 23, 1990

[54] BLOOD FILTER

[75] Inventors: Gary D. Reeder, Morrison; Michael J. Janicki, Aurora, both of Colo.

[73] Assignee: Electromedics, Inc., Englewood, Colo.

[21] Appl. No.: 366,645

[22] Filed: Jun. 14, 1989

[51] Int. Cl.$^5$ .................. B01D 19/00; B01D 27/04; B01D 27/08

[52] U.S. Cl. .................. 210/188; 210/436; 210/446; 210/450; 210/456; 210/457; 210/472; 55/178

[58] Field of Search ............ 210/188, 435, 436, 446, 210/450, 456, 457, 472; 55/178; 604/4, 406

[56] References Cited

U.S. PATENT DOCUMENTS

| Re. 32,711 | 7/1988 | Dickens et al. | 210/436 |
|---|---|---|---|
| 2,712,897 | 7/1955 | Kusserow et al. | |
| 3,701,433 | 10/1972 | Krakauer et al. | 210/446 |
| 3,854,907 | 12/1974 | Rising | 210/436 |
| 3,939,078 | 2/1976 | Servas et al. | 210/436 |
| 3,970,565 | 7/1976 | Ahlstrand et al. | 210/359 |
| 4,038,194 | 7/1977 | Luceyk et al. | 210/436 |
| 4,046,696 | 9/1977 | Mouwen | 210/431 |
| 4,056,476 | 11/1977 | Mouwen et al. | 210/446 |
| 4,157,965 | 6/1979 | Raible | 210/446 |
| 4,243,531 | 1/1981 | Crocket et al. | 210/188 |
| 4,303,530 | 12/1981 | Shah et al. | 210/651 |
| 4,493,705 | 1/1985 | Gordon et al. | 604/4 |
| 4,572,724 | 2/1986 | Rosenberg et al. | 55/178 |
| 4,642,089 | 2/1987 | Zupkas et al. | 55/178 |
| 4,664,682 | 5/1987 | Monzen | 210/188 |
| 4,676,771 | 6/1987 | Henke | 604/4 |
| 4,737,139 | 4/1988 | Zupkas et al. | 55/178 |
| 4,758,337 | 7/1988 | Kohn et al. | 210/188 |
| 4,806,135 | 2/1989 | Siposs | 55/178 |

Primary Examiner—W. Gary Jones
Attorney, Agent, or Firm—Gary M. Polumbus

[57] ABSTRACT

A blood filter device for separating gas bubbles from a flow of blood includes a filter medium in a lower body portion of the device through which the blood must flow before being directed through an outlet tube. An upper cap sealed to the top of the lower body portion includes a blood inlet tube into which a conical dispersion plate is projected so as to decrease the rate of flow of the blood. The rate of flow further decreases as it enters a debubbling chamber in the cap. A top wall of the cap defines a sloped and arched channel around the inlet tube adapted to direct released gas toward a vent tube at the uppermost extent of the sloped top wall.

8 Claims, 2 Drawing Sheets

U.S. Patent    Oct. 23, 1990    Sheet 1 of 2    4,964,984
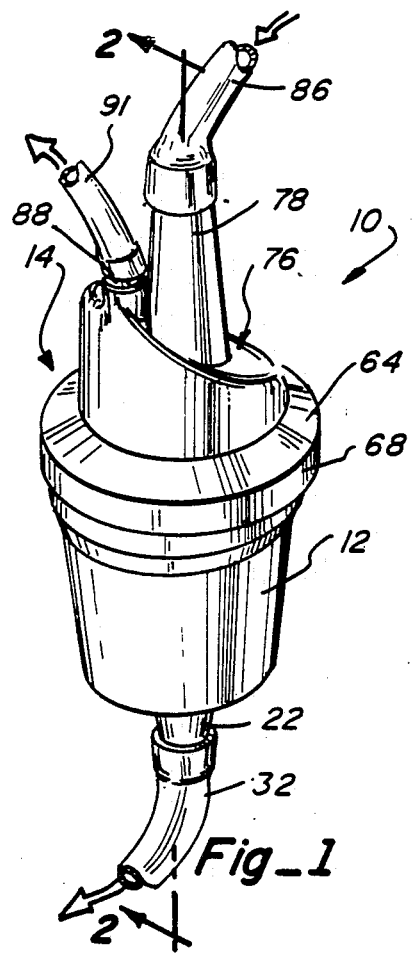
Fig_1
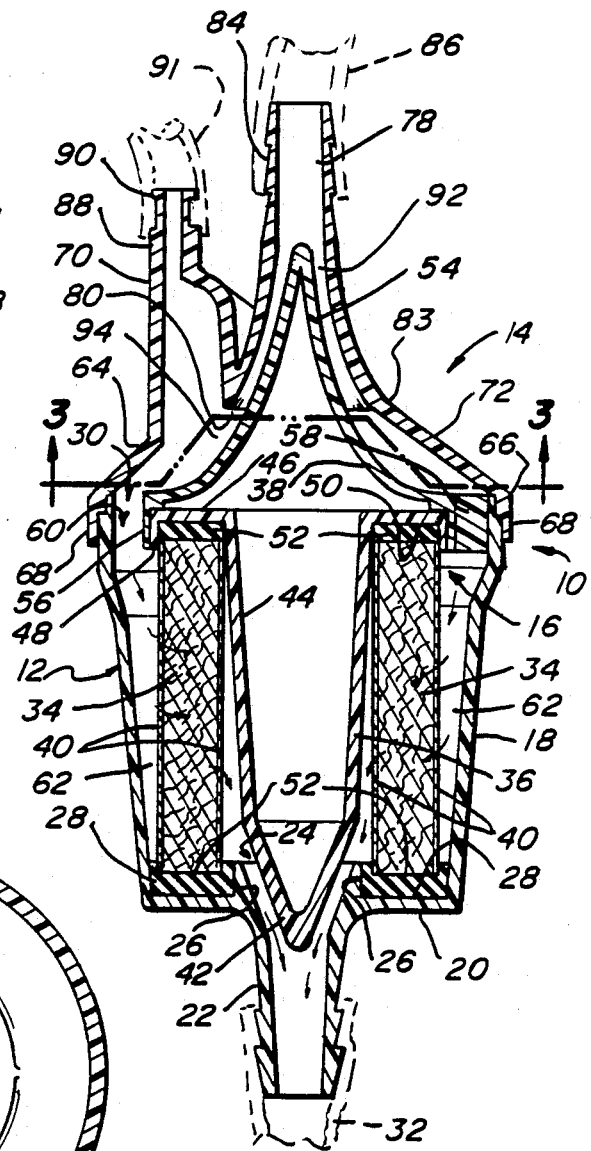
Fig_2
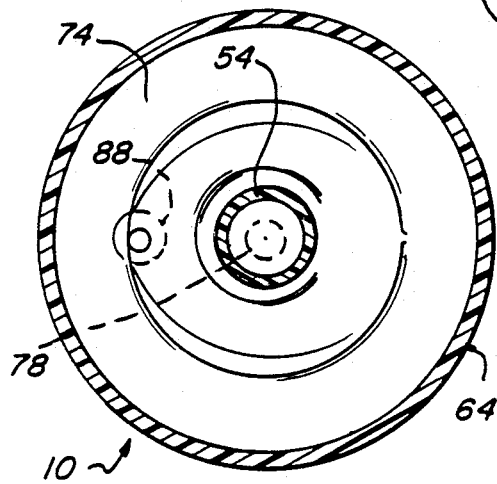
Fig_3

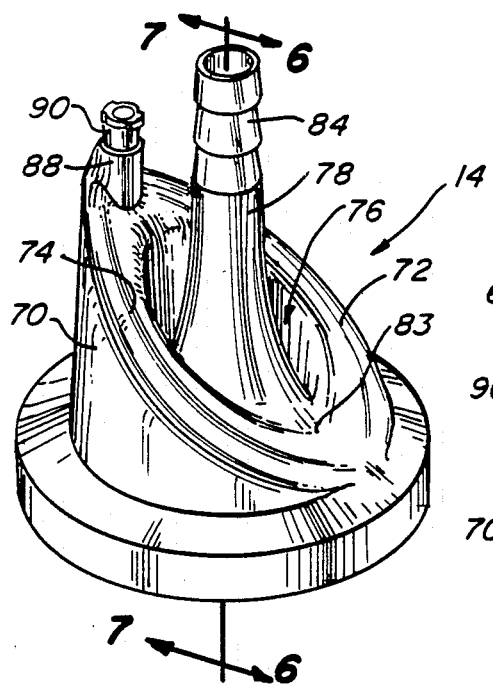
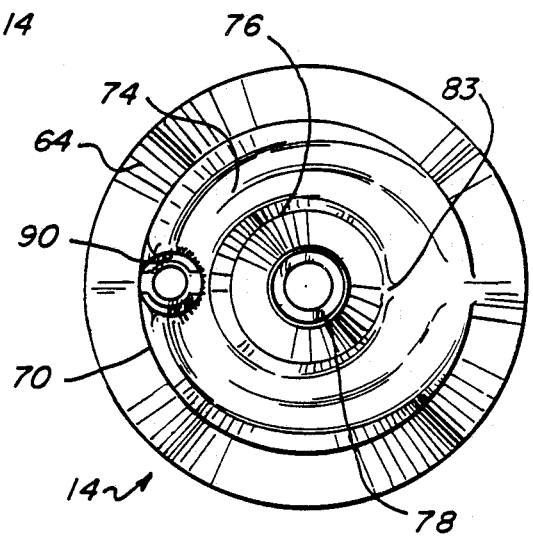
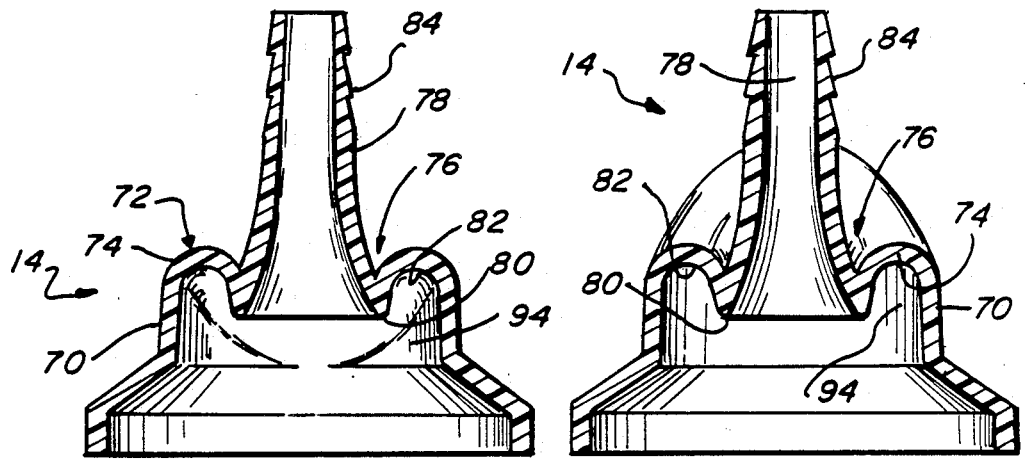
Fig_4  Fig_5
Fig_6  Fig_7

BLOOD FILTER

BACKGROUND OF THE INVENTION

1. Field of the Invention

The present invention relates generally to blood filters and more particularly to a blood filter as may be used in cardiopulmonary bypass surgery having an improved system for removing gas bubbles from the blood.

2. Description of the Prior Art

With the increased frequency of cardiopulmonary bypass surgery and with the recognized need for delivering gas free blood back to the patient, numerous blood filters have been developed. Such filters are used in connection with pump-oxygenator equipment commonly referred to as heart lung machine that are used during open heart surgery. Such surgery, requires that the blood of the patient be shunted around the heart and lungs permitting the surgeon to operate on a heart, whose chambers are relatively free of blood. In operations of this type, it is absolutely essential that all excess gas be removed from the blood before it is returned to the patient or fatal air embolus can occur.

Most filter devices developed for use in cardiopulmonary bypass surgery include a filter screen or mesh of a predetermined size to filter out undesirable elements including gas bubbles whether in the form of micro emboli or gross bubbles. In addition, the housings for some such filters have been designed to further encourage the removal of gas bubbles. For example, in the U.S. patents issued to Johnson & Johnson/Purolator, Inc. U.S. Pat. Nos. 3,939,078, 4,038,194 and 4,046,696, the concept of abruptly decreasing the flow rate of the gas as it enters the filter to release entrained gas is disclosed. Further, these patents disclose the use of a slanted upper wall in the housing to direct gas released from the blood to a vent port in the upper wall. In one of these patents, namely U.S. Pat. No. 3,939,078, the blood inlet to the filter device extends downwardly from the slanted upper wall so as to keep the inflow of blood separate from the gas being removed therefrom which further improves the efficiency of the gas removal by preventing the incoming blood from being mixed with the gas removed from prior blood. U.S. Pat. No. 4,676,771 issued to Henke also broadly recognizes that abruptly slowing the flow rate of blood encourages the release of gas. It will therefore be recognized that ongoing efforts are being exerted toward improving the efficiency with which gas bubbles can be removed from blood before the blood is returned to a patient to diminish the possibility of fatal air embolus.

While the structural features shown to date in the prior art provide improvements over the mere use of a filter medium to remove gas from the blood, it is felt that more efficient systems would be desirable and it is to this end that the present invention has been developed.

SUMMARY OF THE INVENTION

The blood filter of the present invention is of the type that includes a filter medium in a lower portion thereof through which the blood must pass before leaving the filter device and an upper portion or cap for admitting blood to the filter device and directing it to the filter medium. The blood filter is characterized by an improved cap that encourages separation of gas bubbles from the incoming flow of blood so that only minimal, if any, gas bubbles actually pass to the filter medium. The filter medium is of a conventional type that is designed to remove any such gas bubbles, as well as other impurities that may be in the blood, and accordingly the filter device is very efficient in the total removal of gas from a blood flow stream.

The lower body portion of the filter of the present invention is generally cylindrical in configuration having disposed therein a cylindrical filter medium with the filter medium circumscribing an outlet tube that is centrally disposed in the bottom of the lower body. The lower body further defines an annular chamber around the filter medium into which blood is fed from the cap. The cap is hermetically sealed to an open top of the lower body so as to define an enclosure whereby blood entering the device will flow through the cap and into the lower body portion before being filtered and finally emitted through the outlet tube.

The cap includes a vertically oriented inlet tube that is in alignment with a generally conically shaped dispersion plate supported in the filter device in vertical alignment with the filter medium. The dispersion plate protrudes into the inlet tube to receive inflowing blood and disperse it into a conical flow across the dispersion plate. A debubbling chamber is provided around the dispersion plate with a top wall of the cap defining the uppermost extent of the debubbling chamber.

The top wall is uniquely formed and includes an arched channel surrounding the inlet tube and being disposed on an incline to define a continuous passageway whereby gas released from the inflowing blood can be channeled in an accelerated manner out of the filter device through a vent tube provided at the uppermost extent of the arched channel.

The dispersion plate defines a surface over which blood enters the filter device at a predetermined rate and smoothly decelerates towards the debubbling chamber. Upon entering the debubbling chamber which is larger in volume than the space between the dispersion plate and the inlet tube, the blood decelerates to a point which encourages the release of gas bubbles from the blood without creating excessive trauma to the red cells. The gas bubbles rise due to their relatively light weight and are confined in the arched channel which directs the gas around the inlet tube and to the vent tube for removal from the device.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 1 is a perspective view of the blood filter device of the present invention attached to inlet and outlet blood flow tubes as well as a vent tube.

FIG. 2 is an enlarged vertical section taken along line 2—2 of FIG. 1.

FIG. 3 is a section taken along line 3—3 of FIG. 2.

FIG. 4 is a perspective view of the cap of the filter device of the present invention.

FIG. 5 is a top plan view of the filter device of the present invention.

FIG. 6 is a section taken along line 6—6 of FIG. 4.

FIG. 7 is a section taken along line 7—7 of FIG. 4.

DESCRIPTION OF THE PREFERED EMBODIMENT

Looking first at FIGS. 1 and 2, the filter device 10 of the present invention can be seen to include a lower body portion 12, an upper body portion or cap 14 and a central member 16 that is disposed within the lower body portion and protrudes upwardly into the cap. The lower body portion 12 is made of any desirable non-contaminating material such as polycarbonate plastic and while of generally cylindrical configuration actually has a slightly downwardly convergent side wall 18 that is continuous with a bottom wall 20 having an outlet tube 22 surrounding an outlet opening 24 centrally disposed therein. An internally directed raised shoulder 26 circumscribes the outlet opening 24 and defines a circular channel 28 on the bottom wall between the side wall 18 and the raised shoulder 26. The side wall 18 flares outwardly at its upper end defining an open upper end 30. The outlet tube 22 is serrated along its outer surface so as to be capable of hermetically gripping a deformable tube 32 that is attached thereto for removal of filtered blood.

The central member 16 includes a filter medium 34, a directing element 36, and a dispersion plate 38. The filter medium 34 is a cylindrical element preferably in the form of a polyester woven screen and is supported along both its internal and external surfaces by a fan folded screen of a large pore grid possibly made of a polypropylene material.

The directing element 36 is disposed in the hollow interior core of the filter medium 34 and consists of a solid plastic, possibly polycarbonate, element that has a lower conical tip 42, a continuous upper frusto conical wall 44 and an out-turned circular flange 46 having a depending shoulder 48 defining a downwardly opening circular groove 50 at its upper end. The upper end of the filter medium 34 is embedded in a potting compound 52 such as a polyurethane resin and is seated in the downwardly opening circular groove 50 of the directing element 36. The lower end of the filter medium is seated in the circular channel 28 on the bottom wall and again is retained in place with a potting compound 52 such as polyurethane resin.

The dispersion plate 38 is generally conical in configuration having a slight downward and outward flair in the substantially conical side wall 54 thereof. The dispersion plate includes a downturned flange 56 along its lowermost edge which is bonded in any suitable manner, such as by ultrasonic fusion, to the depending shoulder 48 of the directing element.

The central member 16 can therefore be seen to comprise an integrated assembly of the filter medium 34, the directing element 36 and the dispersion plate 38 and is disposed interiorly of the lower body 12 and the cap 14 of the filter device 10. The central member further includes a plurality of integral circumferentially spaced tabs 58 projecting radially from the downward flange 56 of the dispersion plate which are sized to engage the inner surface of the sidewall 18 of the lower body 12 so as to retain a desired spacing between the filter medium and the lower body. The spacer tabs define passageways 60 therebetween so that blood entering the cap 14 of the filter device can readily pass downwardly into an annular chamber 62 surrounding the filter medium 34 and subsequently through the filter medium where it is directed by the directing element 36 into the outlet tube 22. It will be appreciated that the frusto conical wall 44 and conical wall 42 of the directing element define a space between themselves and the filter medium 34 so that blood is free to flow from the device.

The cap 14 includes a frusto conical surface 64 that projects upwardly and inwardly from an outer peripheral edge 66 of the cap and has a downturned flange 68 at the outer peripheral edge. The flange 68 is adapted to be sealed, as by ultrasonic fusion, to the top portion of the side wall 18 of the lower body. A cylindrical vertically oriented wall 70 projects upwardly from the inner edge of the frusto conical wall 64 and has an upper edge that is slanted at approximately a 30 to 40 degree angle relative to the bottom wall 20 of the device 10. A top wall 72 of the cap is disposed along the slanted upper edge of the cylindrical wall 70 and defines a generally circular downwardly concave arched channel 74 around the upper edge of the cylindrical wall. The arched channel 74 surrounds a downwardly convex and generally circular depression 76 in the center of the top wall which in turn surrounds a vertical blood inlet tube 78 for admitting blood to the filter device. As is best seen in FIGS. 2, 6 and 7, the lowermost extent 80 of the inlet tube 78 is below the uppermost extent 82 of the arched channel 74 except at one point location 83 (FIG. 2) where they are coincident. The relationship of the lowermost extent of the inlet tube and the uppermost extent of the arched channel will become more apparent hereinafter. The blood inlet tube 78 is slightly flaired radially outwardly in a downward direction and is continuous with the generally circular depression 76 formed in the top wall 72. Serrations 84 are provided in the outer surface of the inlet tube 78 to hermetically grip a conventional deformable tube 86 through which blood can be passed to the filter device.

A vertically oriented vent tube 88 is formed in the top wall 72 at the uppermost extent of the arcuate channel 74 and includes a connection head 90 for attachment to a conventional luer locking tube 91 to direct vented gas from the device to any desired environment.

It will be appreciated from the above description that the top wall 72 of the cap is formed essentially in the configuration of a donut that has been sliced in half so as to open downwardly and it thereby forms a continuous channel or flow path around the inlet tube 78 for directing gas bubbles to the vent tube 88.

Again with reference to FIG. 2, it will be appreciated that the dispersion plate 38 projects upwardly into the flaired lower end of the blood inlet tube 78 so as to define a generally conical passage 92 between the dispersion plate and the blood inlet tube. The passage 92 is of increased cross-sectional area relative to the upper unobstructed portion of the blood inlet tube so that the flow rate of the blood is decelerated as it passes through the passage 92.

The lower end of the passage 92 is in communication with a debubbling chamber 94 defined between the top wall 72 of the cap and the dispersion plate 38. The debubbling chamber is of appreciably larger volume than the passage 92 between the dispersion plate and the blood inlet tube so that the flow rate of the blood entering the debubbling chamber decreases thereby encouraging gas bubbles entrained in the blood to be released therefrom in a known manner. The blood, of course, is permitted to flow downwardly between the spacer tabs 58 and into the annular chamber 62 around the filter medium 34 before passage through the filter medium and the outlet tube 22 for removal from the filter device. The gas bubbles, on the other hand, which are lighter will tend to migrate upwardly and will be trapped in the arcuate channel 74 around the inlet tube which is sloped so as to conduct and direct the gas efficiently toward the vent tube 88 at the uppermost extent of the arched channel.

Since the lowermost extent of the inlet tube 78 lies below the uppermost extent of the arched channel 74 at all locations other than the one point where they intersect and are coincident at point 83, gas which is released from the blood near the lower end of the slanted top wall 72 can be directed around the inflowing blood stream so as not to intermingle with the inflowing blood but rather will remain separated from the inflowing blood while being conducted toward the vent tube. The lowermost extent of the inlet tube does not project below the uppermost extent of the arched channel at point 83 due to the fact that gas bubbles moving upwardly along the arched channel at this point may get caught on any downward protrusion of the inlet tube and for that reason, the two surfaces at this location are made coincident.

Although the present invention has been described with a certain degree of particularity, it is understood that the present disclosure has been made by way of example, and changes in detail or structure may be made without departing from the spirit of the invention, as defined in the appended claims.

I claim:

1. In a blood filter device for removing gas bubbles from a flow of blood wherein said blood filter has a lower body including a filter medium and an outlet through which blood can flow and an upper body through which the blood passes en route to the lower body, wherein the improvement comprises a cap forming the upper body of the device and being hermetically sealed to the lower body and establishing fluid communication therebetween, said cap having a vertically oriented blood inlet tube, a debubbling chamber in communication with the inlet tube and with the lower body, a vent opening establishing communication between the debubbling chamber and an external environment, and a sloped upper wall of the debubbling chamber passing around the inlet tube, said sloped upper wall defining an inclined arched downwardly concave channel passing around the inlet tube, a lowermost edge of said inlet tube lying beneath the uppermost extent of said arched channel except at a single point location, and wherein the vent opening is positioned in the arched channel at the highest point thereof whereby gas bubbles released from the blood in the debubbling chamber will be encouraged to flow along said arched channel for removal from the device through said vent opening, said device further including a dispersion plate in alignment with the inlet opening for distributing the blood into said debubbling chamber.

2. In a blood filter device for removing gas bubbles from a flow of blood wherein said blood filter has a lower body including a filter medium and an outlet through which blood can flow and an upper body through which the blood passes in route to the lower body, wherein the improvement comprises a cap forming the upper body of the device and being hermetically sealed to the lower body and establishing fluid communication therebetween, said cap having a vertically oriented blood inlet tube, a debubbling chamber in communication with the inlet tube and with the lower body, a vent opening establishing communication between the debubbling chamber and an external environment, and a sloped upper wall of the debubbling chamber passing around the inlet tube, said sloped upper wall defining an inclined arched downwardly concave channel passing around the inlet tube and wherein the vent opening is positioned in the arched channel at the highest point thereof whereby gas bubbles released from the blood in the debubbling chamber will be encouraged to flow along said arched channel for removal from the device through said vent opening, said device further including a dispersion plate in alignment with the inlet opening for distributing the blood into said bubbling chamber, said dispersion plate being conically shaped and having its apex protruding into the inlet tube so as to distribute the blood into the debubbling chamber in a generally conical flow path.

3. In the device of claim 2 wherein the lowermost edge of the inlet tube lies beneath the uppermost extent of said arched channel except at a single point location where they are coincident whereby gas bubbles passing along said arched channel will be substantially segregated from blood entering the debubbling chamber through said inlet tube.

4. In the device of claim 3 wherein said cap is connected to the lower body along a peripheral edge of the cap and wherein the vent opening is spaced inwardly from the peripheral edge of the cap.

5. In the device of claim 3 wherein said cap further includes a generally cylindrical wall extending vertically and having an inclined upper edge, and wherein said arched channel extends along said inclined upper edge of the generally cylindrical wall.

6. In the device of claim 5 wherein said cap has a circular peripheral edge and said generally cylindrical wall is of a smaller diameter than the peripheral edge of said cap.

7. In the device of claim 6 wherein said cap further includes a frustoconical wall connecting the peripheral edge of said cap to the substantially cylindrical wall.

8. In a blood filter device for removing gas bubbles from a flow of blood wherein said device has a lower generally cylindrical body having an open top and a centrally located outlet opening in a bottom thereof, a generally cylindrical filter medium supported in said lower body so as to circumscribe said outlet opening and define an annular chamber around said filter element, a generally conically shaped dispersion plate positioned above the filter element so as to protrude out of the open top of said lower body, and a cap having a circular peripheral edge hermetically sealed to the open top of the lower body with said cap encompassing the dispersion plate, said cap having a vertically oriented blood inlet tube, a debubbling chamber in communication with the inlet tube and surrounding the dispersion plate, said debubbling chamber being in fluid communication with said annular chamber in the lower body, a vent opening establishing communication between the debubbling chamber and an external environment, and a sloped upper wall passing around the inlet tube, said sloped upper wall defining an inclined downwardly concave arched channel passing around the inlet tube a lowermost edge of said inlet tube lying beneath the uppermost extent of said arched channel except at a single point location, and wherein the vent opening is positioned in the arched channel at the highest point thereof whereby gas bubbles released from the blood in the debubbling chamber will be encouraged to flow along said arched channel for removal from the device through said vent opening.

* * * * *

UNITED STATES PATENT AND TRADEMARK OFFICE
CERTIFICATE OF CORRECTION

PATENT NO. : 4,964,984

DATED : October 23, 1990

INVENTOR(S) : Gary D. Reeder and Michael J. Janicki

It is certified that error appears in the above-identified patent and that said Letters Patent is hereby corrected as shown below:

Column 6, line 10, "bubbling" should read --debubbling--.

Signed and Sealed this

Third Day of March, 1992

Attest:

HARRY F. MANBECK, JR.

*Attesting Officer*      *Commissioner of Patents and Trademarks*